(12) United States Patent
Smyth et al.

(10) Patent No.: US 9,492,625 B2
(45) Date of Patent: Nov. 15, 2016

(54) DRY POWDER INHALER WITH FLUTTER DISPERSION MEMBER

(75) Inventors: Hugh D. C. Smyth, West Lake Hill, TX (US); Parthiban Selvam, Lawrence, KS (US); Charles Randall Truman, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 548 days.

(21) Appl. No.: 13/505,402

(22) PCT Filed: Nov. 12, 2010

(86) PCT No.: PCT/US2010/056628
§ 371 (c)(1),
(2), (4) Date: May 31, 2012

(87) PCT Pub. No.: WO2011/060334
PCT Pub. Date: May 19, 2011

(65) Prior Publication Data
US 2012/0234322 A1    Sep. 20, 2012

Related U.S. Application Data

(60) Provisional application No. 61/293,577, filed on Jan. 8, 2010, provisional application No. 61/281,189, filed on Nov. 12, 2009.

(51) Int. Cl.
*A61M 15/00* (2006.01)
*A61M 11/00* (2006.01)

(52) U.S. Cl.
CPC ........ *A61M 15/0028* (2013.01); *A61M 11/003* (2014.02); *A61M 15/0031* (2014.02);
(Continued)

(58) Field of Classification Search
CPC .................... A61M 15/0086; A61M 15/0091; A61M 15/0098; A61M 15/02; A61M 15/0005

USPC ........... 128/203.15, 203.12, 203.19, 200.14, 128/200.16, 200.18
See application file for complete search history.

(56) References Cited

U.S. PATENT DOCUMENTS 16,066 A    11/1856  Murphy
361,748 A    4/1867  Culbertson
(Continued)

FOREIGN PATENT DOCUMENTS

EP    1 291 032 A2    3/2003
EP    1 658 872 A2    5/2006
(Continued)

OTHER PUBLICATIONS

Crowder, T., et al., "2001: An Odyssey in Inhaler Formulation and Design," Pharmaceutical Technology, Jul. 2001, 9 pages.
(Continued)

*Primary Examiner* — Tan-Uyen (Jackie) T Ho
*Assistant Examiner* — Joseph D Boecker
(74) *Attorney, Agent, or Firm* — Schwegman Lundberg & Woessner, P.A.

(57) ABSTRACT

A dry powder inhaler including a housing defining a chamber for receiving a dose of powdered medicament, an inhalation port in fluid communication with the chamber, at least one airflow inlet providing fluid communication between the chamber and an exterior of the housing, and a flutter element in the chamber and associated with a dose of powdered medicament. The flutter element has a tensioned distal end proximate the at least one airflow inlet and a free proximal end opposite to the distal end and downstream of the inlet. The flutter element is configured to vibrate in response to airflow through the chamber and aerosolize the dose of powdered medicament.

18 Claims, 6 Drawing Sheets

(52) U.S. Cl.
CPC ..... *A61M15/0038* (2014.02); *A61M 15/0086* (2013.01); *A61M 2202/064* (2013.01); *A61M 2205/0233* (2013.01); *A61M 2206/16* (2013.01)

(56) References Cited

U.S. PATENT DOCUMENTS

| | | | |
|---|---|---|---|
| 263,451 A | 8/1882 | Adams | |
| 376,819 A | 1/1888 | Glew | |
| 419,942 A | 1/1890 | Harding | |
| 598,286 A | 2/1898 | Curran | |
| 631,621 A | 8/1899 | Curran | |
| 658,436 A | 9/1900 | Groth | |
| 844,097 A | 2/1907 | Caldwell | |
| 1,599,959 A | 9/1926 | Fujimoto | |
| 1,752,956 A | 4/1930 | Lex | |
| 2,214,032 A | 9/1940 | Stewart | |
| 2,470,296 A | 5/1949 | Fields | |
| 2,513,145 A | 6/1950 | Chapple | |
| 2,517,482 A | 8/1950 | Hall | |
| 2,534,636 A | 12/1950 | Stirn | |
| 2,549,303 A | 4/1951 | Friden | |
| 2,573,918 A | 11/1951 | McCuiston | |
| 2,581,182 A | 1/1952 | Fields | |
| 2,587,215 A | 2/1952 | Priestly | |
| 2,603,215 A | 7/1952 | Arnow | |
| 2,603,216 A | 7/1952 | Taplin et al. | |
| 2,622,594 A | 12/1952 | Brooks | |
| 2,641,255 A | 6/1953 | Leonaitis | |
| 2,642,063 A | 6/1953 | Brown | |
| 2,672,865 A | 3/1954 | Willis | |
| 2,693,805 A | 11/1954 | Taplin et al. | |
| 2,992,645 A | 7/1961 | Fowler | |
| 3,105,488 A | 10/1963 | Richards | |
| 3,518,992 A | 7/1970 | Altounyan et al. | |
| 3,635,219 A | 1/1972 | Altounyan et al. | |
| 3,807,400 A | 4/1974 | Cocozza | |
| 3,837,341 A | 9/1974 | Bell | |
| 3,858,583 A | 1/1975 | Hallworth et al. | |
| 3,870,046 A | 3/1975 | Elliott | |
| 3,888,252 A | 6/1975 | Side et al. | |
| 3,888,253 A * | 6/1975 | Watt | A61M 15/0028 128/203.15 |
| 3,906,950 A | 9/1975 | Cocozza | |
| 3,921,637 A | 11/1975 | Bennie et al. | |
| 3,948,264 A | 4/1976 | Wilke et al. | |
| 3,964,483 A | 6/1976 | Mathes | |
| 3,971,377 A | 7/1976 | Damani | |
| 3,980,074 A | 9/1976 | Watt et al. | |
| 3,991,761 A | 11/1976 | Cocozza | |
| 4,013,075 A | 3/1977 | Cocozza | |
| 4,090,642 A | 5/1978 | Baker | |
| 4,147,166 A | 4/1979 | Hansen | |
| 4,216,768 A | 8/1980 | Jack | |
| 4,338,931 A | 7/1982 | Cavazza | |
| 4,353,365 A | 10/1982 | Hallworth et al. | |
| 4,524,769 A | 6/1985 | Wetterlin | |
| 4,570,630 A | 2/1986 | Elliott et al. | |
| 4,735,358 A | 4/1988 | Morita et al. | |
| 4,841,964 A | 6/1989 | Hurka et al. | |
| 4,860,740 A | 8/1989 | Kirk et al. | |
| 4,907,583 A | 3/1990 | Wetterlin et al. | |
| 5,033,463 A | 7/1991 | Cocozza | |
| 5,035,237 A | 7/1991 | Newell et al. | |
| 5,042,472 A | 8/1991 | Bunin | |
| 5,161,524 A | 11/1992 | Evans | |
| 5,186,164 A | 2/1993 | Raghuprasad | |
| 5,201,308 A | 4/1993 | Newhouse | |
| 5,239,991 A | 8/1993 | Chawla et al. | |
| 5,239,992 A | 8/1993 | Bougamont et al. | |
| 5,239,993 A | 8/1993 | Evans | |
| 5,327,883 A | 7/1994 | Williams et al. | |
| 5,347,999 A | 9/1994 | Poss et al. | |
| 5,349,947 A | 9/1994 | Newhouse et al. | |
| 5,372,128 A | 12/1994 | Haber et al. | |
| 5,388,572 A | 2/1995 | Mulhauser et al. | |
| 5,394,868 A | 3/1995 | Ambrosio et al. | |
| 5,408,994 A | 4/1995 | Wass et al. | |
| 5,415,162 A | 5/1995 | Casper et al. | |
| 5,429,122 A | 7/1995 | Zanen et al. | |
| 5,437,270 A | 8/1995 | Braithwaite | |
| 5,437,271 A | 8/1995 | Hodson et al. | |
| 5,469,843 A | 11/1995 | Hodson | |
| 5,476,093 A | 12/1995 | Lankinen | |
| 5,482,032 A | 1/1996 | Smith et al. | |
| 5,503,144 A | 4/1996 | Bacon | |
| 5,505,196 A | 4/1996 | Herold et al. | |
| 5,522,383 A | 6/1996 | Calvert et al. | |
| 5,533,502 A | 7/1996 | Piper | |
| 5,546,932 A | 8/1996 | Galli | |
| 5,575,280 A | 11/1996 | Gupte et al. | |
| 5,590,645 A | 1/1997 | Davies et al. | |
| 5,595,175 A | 1/1997 | Malcher et al. | |
| 5,615,670 A | 4/1997 | Rhodes | |
| 5,617,844 A * | 4/1997 | King | A61M 15/0086 128/200.14 |
| 5,619,984 A | 4/1997 | Hodson et al. | |
| 5,628,307 A | 5/1997 | Clark et al. | |
| 5,651,359 A | 7/1997 | Bougamont et al. | |
| 5,653,227 A | 8/1997 | Barnes et al. | |
| 5,655,523 A | 8/1997 | Hodson et al. | |
| 5,657,749 A | 8/1997 | Cox | |
| 5,669,378 A | 9/1997 | Pera et al. | |
| 5,673,685 A | 10/1997 | Heide et al. | |
| 5,673,686 A | 10/1997 | Villax et al. | |
| 5,687,912 A * | 11/1997 | Denyer | A61M 11/06 128/200.21 |
| 5,692,496 A | 12/1997 | Casper et al. | |
| 5,694,920 A | 12/1997 | Abrams et al. | |
| 5,699,789 A | 12/1997 | Hendricks | |
| 5,724,959 A | 3/1998 | McAughey et al. | |
| 5,740,793 A | 4/1998 | Hodson et al. | |
| 5,743,250 A | 4/1998 | Gonda et al. | |
| 5,752,505 A | 5/1998 | Ohki et al. | |
| 5,775,320 A | 7/1998 | Patton et al. | |
| 5,787,881 A | 8/1998 | Chawla | |
| 5,813,401 A * | 9/1998 | Radcliff | A61M 16/208 128/200.14 |
| 5,829,434 A | 11/1998 | Ambrosio et al. | |
| 5,857,456 A | 1/1999 | Sun et al. | |
| 5,860,419 A | 1/1999 | Davies et al. | |
| 5,875,776 A | 3/1999 | Vaghefi | |
| 5,881,719 A | 3/1999 | Gottenauer et al. | |
| 6,026,809 A | 2/2000 | Abrams et al. | |
| 6,029,663 A | 2/2000 | Eisele et al. | |
| 6,065,472 A | 5/2000 | Anderson et al. | |
| 6,071,498 A | 6/2000 | Narodylo et al. | |
| 6,089,227 A | 7/2000 | Nilsson | |
| 6,098,619 A | 8/2000 | Britto et al. | |
| 6,123,070 A * | 9/2000 | Bruna | A61M 15/0065 128/203.12 |
| 6,138,673 A | 10/2000 | Shepherd | |
| 6,152,130 A | 11/2000 | Abrams et al. | |
| 6,182,655 B1 | 2/2001 | Keller et al. | |
| 6,230,707 B1 | 5/2001 | Hörlin | |
| 6,234,169 B1 | 5/2001 | Bulbrook et al. | |
| 6,237,590 B1 | 5/2001 | Leedom et al. | |
| 6,237,591 B1 | 5/2001 | Jackson | |
| 6,257,233 B1 | 7/2001 | Burr et al. | |
| 6,286,507 B1 | 9/2001 | Jahnsson | |
| 6,328,033 B1 | 12/2001 | Avrahami | |
| 6,378,519 B1 | 4/2002 | Davies et al. | |
| 6,425,888 B1 | 7/2002 | Embleton et al. | |
| 6,427,688 B1 | 8/2002 | Ligotke et al. | |
| 6,484,718 B1 | 11/2002 | Schaeffer et al. | |
| 6,521,260 B1 | 2/2003 | Staniforth | |
| 6,561,186 B2 | 5/2003 | Casper et al. | |
| 6,626,173 B2 | 9/2003 | Genova et al. | |
| 6,651,341 B1 | 11/2003 | Myrman et al. | |
| 6,655,380 B1 | 12/2003 | Andersson et al. | |
| 6,655,381 B2 | 12/2003 | Keane et al. | |
| 6,698,425 B1 | 3/2004 | Widerström | |
| 6,715,486 B2 | 4/2004 | Gieschen et al. | |
| 6,752,147 B1 | 6/2004 | Goldemann et al. | |

(56) References Cited

U.S. PATENT DOCUMENTS

| | | |
|---|---|---|
| 6,779,520 B2 | 8/2004 | Genova et al. |
| 6,780,508 B1 | 8/2004 | Caponetti et al. |
| 6,810,872 B1 | 11/2004 | Ohki et al. |
| 6,840,239 B2 | 1/2005 | Myrman |
| 6,889,690 B2 | 5/2005 | Crowder et al. |
| 6,971,383 B2 | 12/2005 | Hickey et al. |
| 6,983,748 B2 | 1/2006 | Brown et al. |
| 7,011,818 B2 | 3/2006 | Staniforth |
| 7,025,056 B2 | 4/2006 | Eason et al. |
| 7,032,593 B2 | 4/2006 | Johnston et al. |
| 7,069,929 B2 | 7/2006 | Young et al. |
| 7,107,988 B2 | 9/2006 | Pinon et al. |
| 7,118,010 B2 | 10/2006 | Crowder et al. |
| 7,228,860 B2 | 6/2007 | Andersson et al. |
| 7,252,087 B2 | 8/2007 | Wachtel |
| 7,278,425 B2 | 10/2007 | Edwards et al. |
| 7,284,553 B2 | 10/2007 | Hochrainer |
| 7,401,713 B2 | 7/2008 | Ede et al. |
| 7,556,035 B2 | 7/2009 | Young et al. |
| 7,617,822 B2 | 11/2009 | De Boer et al. |
| 7,718,163 B2 | 5/2010 | Staniforth |
| 7,735,485 B2 | 6/2010 | Yamashita et al. |
| 7,810,494 B2 | 10/2010 | Harmer et al. |
| 7,958,890 B2 | 6/2011 | Gieschen et al. |
| 8,037,880 B2 | 10/2011 | Zhu et al. |
| 8,127,763 B2 * | 3/2012 | Smyth ............... A61M 15/0028 128/200.24 |
| 2004/0094152 A1 | 5/2004 | Harvey et al. |
| 2004/0206773 A1 | 10/2004 | Ede et al. |
| 2004/0244794 A1 | 12/2004 | Richards |
| 2005/0172962 A1 | 8/2005 | Gumaste et al. |
| 2005/0194008 A1 | 9/2005 | Andersson et al. |
| 2006/0191534 A1 | 8/2006 | Hickey |
| 2007/0209661 A1 | 9/2007 | Smyth et al. |
| 2007/0215149 A1 | 9/2007 | King et al. |
| 2008/0035143 A1 | 2/2008 | Sievers |
| 2008/0078689 A1 | 4/2008 | Pentafragas |
| 2008/0202514 A1 | 8/2008 | Kriksunov |
| 2008/0314384 A1 | 12/2008 | Harris et al. |
| 2009/0084379 A1 | 4/2009 | Goeckner et al. |
| 2009/0095294 A1 | 4/2009 | Smyth |
| 2009/0165790 A1 | 7/2009 | Crowder et al. |
| 2009/0178676 A1 | 7/2009 | Villax et al. |
| 2009/0250058 A1 | 10/2009 | Lastow et al. |
| 2009/0308392 A1 | 12/2009 | Smutney et al. |
| 2009/0320838 A1 | 12/2009 | Malhotra et al. |
| 2010/0051023 A1 * | 3/2010 | Kladders ........... A61M 15/0028 128/200.21 |
| 2010/0059049 A1 | 3/2010 | Genosar |
| 2010/0059051 A1 * | 3/2010 | Kladders ........... A61M 15/0065 128/203.15 |
| 2010/0300440 A1 | 12/2010 | Deboeck et al. |
| 2010/0326438 A1 | 12/2010 | Dunne |
| 2011/0120467 A1 | 5/2011 | Pardonge |
| 2013/0032145 A1 * | 2/2013 | Adler ................ A61M 15/0028 128/203.15 |

FOREIGN PATENT DOCUMENTS

| | | | |
|---|---|---|---|
| GB | 2334686 A | * | 9/1999 |
| JP | 2002537952 A | | 11/2002 |
| WO | 2006/031775 A2 | | 3/2006 |
| WO | WO-2011060334 | | 5/2011 |

OTHER PUBLICATIONS

Hickey, A., et al., "A New Millennium for Inhaler Technology," Pharmaceutical Technology, Jun. 1997, 7 pages.

Martonen, T., et al., "Issues in Drug Delivery: Concepts and Practice," Respiratory Care, Sep. 2005, vol. 50, No. 9, 25 pages.

Peart, J., et al., "New Developments in Dry Powder Inhaler Technology," American Pharmaceutical Review, 2001, vol. 4, 7 pages.

Prime, D., et al., "Review of Dry Powder Inhalers," Advanced Drug Delivery Reviews, 1997, vol. 26, 8 pages.

Smyth, H., et al., "Carriers in Drug Powder Delivery—Implications for Inhalation System Design," American Journal of Drug Delivery, 2005, vol. 3, Iss. 2, 17 pages.

Japanese Patent Office, Official Action for Japanese Application No. 2008-558311 dated Jan. 19, 2012, 5 pages.

"International Application Serial No. PCT/US201/056628, International Preliminary Report on Patentability mailed May 24, 2012", 4 pgs.

"International Application Serial No. PCT/US2010/056628, International Search Report mailed Jul. 29, 2011", 3 pgs.

"International Application Serial No, PCT/US2010/056628, Written Opinion mailed Jul. 29, 2011", 3 pgs.

* cited by examiner

DRY POWDER INHALER WITH FLUTTER DISPERSION MEMBER

CROSS-REFERENCE TO RELATED APPLICATIONS

This application claims the benefit of priority of U.S. provisional application No. 61/281,189, entitled "Inhaler with a Different Mode of Flutter Operation," filed on Nov. 12, 2009, and U.S. provisional application No. 61/293,577, entitled "Inhaler Apparatus and Method of Making and Using the Same," filed on Jan. 8, 2010, the contents of both of which are incorporated herein by reference in their entirety.

TECHNICAL FIELD

The present invention is directed generally to inhalers, for example, dry powder inhalers, and methods of delivering a medicament to a patient. More particularly, the present invention is directed to dry powder inhalers having a flutter dispersion member.

BACKGROUND

Dry powder inhalers ("DPIs") represent a promising alternative to pressurized meted dose inhaler ("pMDI") devices for delivering drug aerosols without using CFC propellants. See generally, Crowder et al., 2001: an Odyssey in Inhaler Formulation and Design, Pharmaceutical Technology, pp. 99-113, July 2001; and Peart et al., New Developments in Dry Powder Inhaler Technology, American Pharmaceutical Review, Vol. 4, n, 3, pp. 37-45 (2001). Martonen et al. 2005 Respiratory Care, Smyth and Hickey American Journal of Drug Delivery, 2005.

Typically, the DPIs are configured to deliver a powdered drug or drug mixture that includes an excipient and/or other ingredients. Conventionally, many DPIs have operated passively, relying on the inspiratory effort of the patient to dispense the drug provided by the powder. Unfortunately, this passive operation can lead to poor dosing uniformity since inspiratory capabilities can vary from patient to patient, and sometimes even use-to-use by the same patient, particularly if the patient is undergoing an asthmatic attack or respiratory-type ailment which tends to close the airway.

Generally described, known single and multiple dose DPI devices use: (a) individual pre-measured doses, such as capsules containing the drug, which can be inserted into the device prior to dispensing; or (b) bulk powder reservoirs which are configured to administer successive quantities of the drug to the patient via a dispensing chamber which dispenses the proper dose. See generally, Prime et al., Review of Dry Powder Inhaler's, 26 Adv. Drug Delivery Rev., pp. 51-58 (1997); and Hickey et al., A new millennium for inhaler technology, 21 Pham. Tech., n. 6, pp. 116-125 (1997).

In operation, DPI devices desire to administer a uniform aerosol dispersion amount in a desired physical form (such as a particulate size) of the dry powder into a patient's airway and direct it to a desired deposit site. If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform aerosol dispersion. In addition, as noted above, many dry powder formulations employ larger excipient particles to promote flow properties of the drug. However, separation of the drug from the excipient, as well as the presence of agglomeration, can require additional inspiratory effort, which, again, can negatively impact the aerosol dispersion of the powder within the air stream of the patient. Inadequate dispersions may inhibit the drug from reaching its preferred deposit/destination site and can prematurely deposit undue amounts of the drug elsewhere.

Further, many dry powder inhalers can retain a significant amount of the drug within the device, which can be especially problematic over time. Typically, this problem requires that the device be disassembled and cleansed to assure that it is in proper working order. In addition, the hygroscopic nature of many of these dry powder drugs may also require that the device be cleansed and dried periodically.

In recent years, dry powder inhalers (DPIs) have gained widespread use, particularly in the United States. Currently, the DPI market is estimated to be worth in excess of $4 billion. Dry powder inhalers have the added advantages of a wide range of doses that can be delivered, excellent stability of drugs in powder form (no refrigeration), ease of maintaining sterility, non-ozone depletion, and they require no press-and-breathe coordination.

There is great potential for delivering a number of therapeutic compounds via the lungs (see, for example, Martonen T., Smyth H D C, Isaacs K., Burton R., "Issues in Drug Delivery: Dry Powder Inhaler Performance and Lung Deposition": Respiratory Care. 2005, 50(9); and Smyth H D C, Hickey, A J, "Carriers in Drug Powder Delivery: Implications for Inhalation System Design," American Journal of Drug Delivery, 2005, 3(2), 117-132). In the search for non-invasive delivery of biologics (which currently must be injected), it was realized that the large highly absorptive surface area of the lung with low metabolic drug degradation, could be used for systemic delivery of proteins such as insulin. The administration of small molecular weight drugs previously administered by injection is currently under investigation via the inhalation route either to provide non-invasive rapid onset of action, or to improve the therapeutic ratio for drugs acting in the lung (e.g. lung cancer). Gene therapy of pulmonary disease is still in its infancy but could provide valuable solutions to currently unmet medical needs Key to all inhalation dosage forms is the need to maximize the "respirable dose" (particles with aerodynamic diameters <5.0 μm that deposit in the lung) of a therapeutic agent and reduce variability in dosing. However, both propellant-based inhalers and current DPI systems only achieve lung deposition efficiencies of less than 30% of the delivered dose. The primary reason why powder systems have limited efficiency is the difficult balancing of particle size (particles under 5 μm diameter) and strong inter-particulate forces that prevent deaggregation of powders (strong cohesive forces begin to dominate at particle sizes <10 μm) (Smyth H D C., Hickey, A J., "Carriers in Drug Powder Delivery: Implications for inhalation System Design," American Journal of Drug Delivery, 2005, 3(2), 117-132). Thus, DPIs require considerable inspiratory effort to draw the powder formulation from the device to generate aerosols for efficient lung deposition (see FIG. 1 for an illustration of typical mechanism of powder dispersion for DPIs). Many patients, particularly asthmatic patients, children, and elderly patients, which are important patient groups for respiratory disease, are not capable of such effort. In most DPIs, approximately 60 L/min of airflow is required to effectively deaggregate the fine cohesive powder. All currently available DPIs suffer from this potential drawback.

Multiple studies have shown that the dose emitted from dry powder inhalers (DPI) is dependent on air flow rates (see Martonen T., Smyth H D C, Isaccs K., Burton R., "Issues in Drug Delivery: Dry Powder Inhaler Performance and Lung Deposition": Respiratory Care. 2005, 50(9)). Increasing air-flow increases drug dispersion due to increases in drag forces of the fluid acting on the particle located in the flow. The Turbuhaler® device (a common DPI), is not suitable for children because of the low flow achieved by this patient group (see Martonen T., Smyth H D C, Isaccs K., Burton R., "Issues in Drug Delivery: Dry Powder Inhaler Performance and Lung Deposition": Respiratory Care. 2005, 50(9)).

Considerable intra-patient variability of inhalation rates has been found when patients inhale through two conventional DPI devices. That inherent variability has prompted several companies to evaluate ways of providing energy in the inhaler (i.e. "active" DPIs). Currently, there is no active DPI commercially available. The active inhalers under investigation include technologies that use compressed air, piezoelectric actuators, and electric motors. The designs of those inhalers are very complex and utilize many moving parts and components. The complexity of those devices presents several major drawbacks including high cost, component failure risk, complex manufacturing procedures, expensive quality control, and difficulty in meeting specifications for regulatory approval and release (Food and Drug Administration).

Alternatively, powder technology provides potential solutions for flow rate dependence of DPIs. For example, hollow porous microparticles having a geometric size of 5-30 µm, but aerodynamic sizes of 1-5 µm require less power for dispersion than small particles of the same mass. This may lead to flow independent drug dispersion but is likely to be limited to a few types of drugs with relevant physicochemical properties.

Thus there are several problems associated with current dry powder inhaler systems including the most problematic issue: the dose a patient receives is highly dependent on the flow rate the patient can draw through the passive-dispersion device. Several patents describing potential solutions to this problem employ an external energy source to assist in the dispersion of powders and remove this dosing dependence on patient inhalation characteristics. Only one of these devices has made it to market or been approved by regulatory agencies such as the US Food and Drug Administration and the same device has subsequently been removed from the market. Even upon approval, it is likely that these complex devices will have significant costs of manufacture and quality control, which could have a significant impact on the costs of drugs to patients.

The present disclosure describes exemplary dry powder inhalers and associated single or multi-dose packaging, which holds the compound to be delivered for inhalation as a dry powder. These dry powder inhalers bridge the gap between passive devices and active devices. The inhalers are passive devices that operate using the energy generated by the patient inspiratory flow inhalation maneuver. However, the energy generated by airflow within the devices is focused on the powder by using oscillations induced by airflow across an element within the inhaler. This film or web element flutters with considerable energy and velocities to detach the drug coated on the element such that it can be aerosolized and inhaled. In this way the inhalers can be "tuned" to disperse the powder most efficiently by adjusting the resonance frequencies of the elastic element to match the physicochemical properties of the powder. In addition, the airflow rate required to generate the appropriate oscillations within the device is minimized because the energy that is harnessed by the flutter member from the inhalation flow is used to create the vibrations in the elastic element that is in direct contact with the micronized drug powder. Inhaler performance may be tailored to the lung function of individual patients by modulating the film properties, drug particle properties, and degree of coating of the particles on the film. Thus, even patients with poor lung function and those who have minimal capacity to generate airflow during inspiration will able to attain the flow rate required to induce oscillations in the flutter element.

SUMMARY OF THE INVENTION

In accordance with various exemplary aspects of the disclosure, a dry powder inhaler may include a housing defining a chamber for receiving a dose of powdered medicament, an inhalation port in fluid communication with the chamber, at least one airflow inlet providing fluid communication between the chamber and an exterior of the housing, and a flutter element in the chamber and associated with a dose of powdered medicament. The flutter element has a tensioned distal end proximate the at least one airflow inlet and a free proximal end opposite to the distal end and downstream of the inlet. The flutter element is configured to vibrate in response to airflow through the chamber and aerosolize the dose of powdered medicament.

According to various exemplary aspects, a method for delivering medicament to a patient may include tensioning a distal end of a flutter element at a distal end of a dosing chamber of a dry powder inhaler while permitting a proximal end of the flutter element to remain free of tension, exposing the flutter element, including a dose of powdered medicament, to a flow of air through the dry powder inhaler, inducing vibrations in the flutter element so as to aerosolize the dose of powdered medicament, and directing the flow of air with the aerosolized dose of powdered medicament to an outlet port of the dry powder inhaler.

In some exemplary aspects, a dry powder inhaler for delivering medicament to a patient may include a housing defining a chamber and an inhalation port in fluid communication with the chamber. The inhaler may comprise a flutter element in the chamber and associated with a dose of powdered medicament. The flutter element may have a tensioned distal end proximate the at least one airflow inlet and a free proximal end opposite to the distal end and downstream of the inlet. The flutter element may be configured to vibrate in response to airflow through the chamber and aerosolize the dose of powdered medicament.

DETAILED DESCRIPTION

Figure 1:
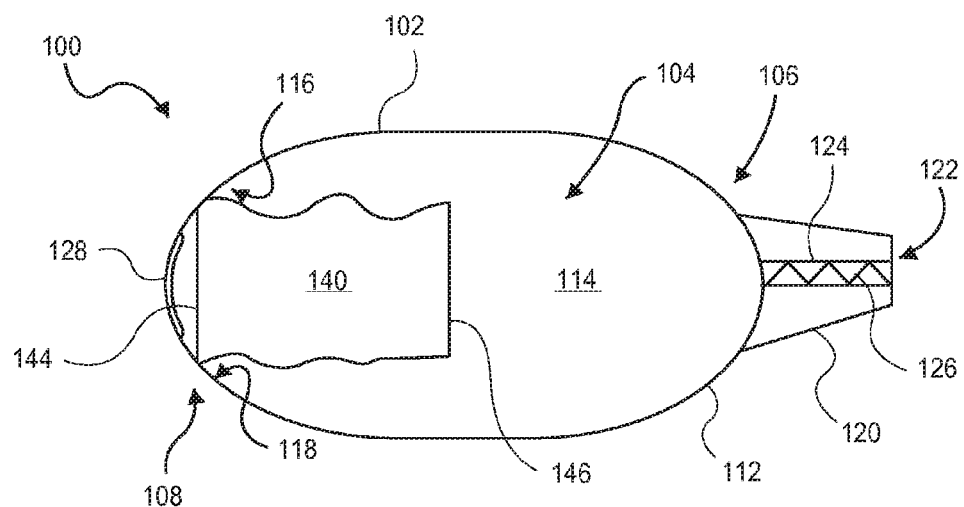
FIG. 1 is a schematic representation of a top cross-sectional view of an exemplary inhaler in accordance with various aspects of the disclosure.
Figure 2:
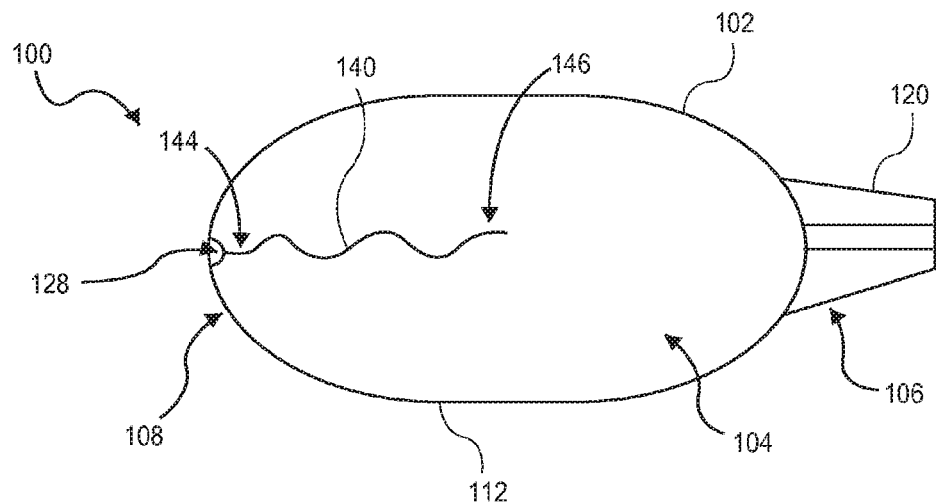
FIG. 2 is a schematic representation of a side cross-sectional view of the inhaler of FIG. 1.

An exemplary embodiment of a dry powder inhaler 100 is illustrated in FIGS. 1 and 2. According to various aspects of the disclosure, the dry powder inhaler 100 may comprise a housing 102 defining a chamber 104. A proximal end 106 of the housing 102 may include a mouthpiece 120. In some aspects, the mouthpiece 120 may comprise a separate structure affixed to an outer wall 112 of the housing 102. In some aspects, the mouthpiece 120 and housing 102 may comprise a single piece of unitary construction.

The mouthpiece 120 may include an opening 122 providing fluid communication between the chamber 104 and the outside of the housing 102 (i.e., ambient air). The opening 122 may be shaped as an oval, a circle, a triangle, or any other desired shape. The mouthpiece 120 may have a shape that facilitates pursing of a patient's lips over the mouthpiece 120 and creating a seal between the lips and the mouthpiece 120.

In various aspects, the inhaler 100 may include a nozzle 124 between the chamber 104 and the opening 122. According to various aspects, the nozzle 124 may extend from the opening 122, through the mouthpiece 120, and into the chamber 104. In some aspects, the nozzle 124 may comprise at least one helical tube 126 through which air and powder can be inhaled. The tube 126 can be configured to increase the turbulence in the air that flows through the nozzle 124. According to various aspects, the mouthpiece 120 and/or the housing 102 may include a mesh, screen, or the like (not shown) to prevent undesirably large particles, such as, for example, carrier particles, from exiting the inhaler 100 and entering a user's mouth and/or airways.

In accordance with various aspects, a distal end 108 of the housing 102 may include one or more airflow inlets 128 providing fluid communication between the chamber 104 and ambient air outside the housing 102. A flutter element 140 may extend across a center region 114 of the chamber 104 at or near the inlets and at or near the wall of the distal end 108 of the housing. In some aspects, the flutter element 140 may extend between opposing inner walls 116, 118 of the housing 102. According to various aspects, the airflow inlets 128 may be shaped as elongated slots, and the flutter element 140 may be arranged such that the planar surfaces of the flutter element 140 extend substantially parallel with the longitudinal direction of the elongated slot. As such, airflow through the chamber 104 may flow above and/or below the flutter element 140 depending on whether the flutter element 140 is positioned at the bottom of the slot, the middle of the slot, or the top of the slot.

The flutter element 140 may be pre-coated with a dose of a medicament, for example, a dose of powdered medicament, and the center region 114 may comprise a region for dispensing a dose of medicament into airflow through the inhaler 100. In some aspects, the powdered particles are tightly bound to the flutter element 140 such that the particles remain substantially on the flutter element 140 until used for an inhalation dose. Contact of the coated flutter element 140 with surfaces of the inhaler assembly and/or packaging should not impact the dosage.

The term "medicament" as used throughout this disclosure may include one or more drugs and/or compositions for treatment. For example, the flutter element 140 may be coated with a medicament containing two or more drugs mixed together. In some aspects, two or more drugs may be coated onto the flutter element 140 in a side-by-side manner or any other pattern. In some aspects, the chamber 104 may be divided into compartments, and each compartment may contain a separate flutter element 140 with the same or different medicament and/or drug(s) coated thereon. In some aspects, the chamber 104 may be divided into compartments, and each compartment may contain a portion of the same flutter element 140, with each portion having the same or different medicament and/or drug(s) coated thereon.

According to some aspects, the flutter element 140 may comprise a membrane 142, for example, a thin elastic membrane, and in some aspects an aeroelastic membrane. In accordance with some aspects, the flutter element 140 may comprise a membrane, a film, a reed, a sheet, a panel, or a blade. The flutter element 140 may be manufactured of materials comprising polymers, thin metals, and/or metal-coated polymers. In some aspects, the flutter element 140 may be inserted into the inhaler 100, used, and then discarded. In some aspects, the entire inhaler may be disposed of after a single use. It should be appreciated that the flutter element 140 can be made thicker and/or more rigid to reduce the degree to which the flutter element 140 will droop in the absence of airflow due to the force of gravity. A more rigid and/or thicker flutter element 140 may result in less flutter insofar as amplitude and wavelength, but at a higher frequency.

According to various aspects, a first end 144 of the element 140 is proximate the airflow inlet 128 at the distal end 108 of the housing 102. The first end 144 of the element 140 is held substantially taut across the chamber 104. A second end 146 of the element 140, opposite to the first end 144, is left free as it extends towards the proximal end 106 of the housing 102. Thus, the element 140 is free to flutter, for example, like a flag, as air flows through the chamber 104 from the airflow inlet 128 to the mouthpiece 120.

It should be appreciated that the first end 144 of the element 140 may be held by any known structure and method. For example, the element 140 may be coupled to the housing 102 in tension via clipping, gluing, adhering, bonding, molding, fusing, or the like. In some aspects, the housing 102 may comprise top and bottom shells (not shown), and the first end 144 of the element 140 may be sandwiched between the shells in a substantially taut configuration, while the second end 146 is left free to flutter in airflow or droop in the absence of airflow. It would be understood by a person skilled in the art that the amount of droop would depend on the material and composition of the element 140.

The tensioning of a leading end of the flutter element (with respect to airflow direction) while leaving the opposite end free may provide performance increases over a fully-tensioned flutter element due to improved energy transfer into the powder coating the film. For example, velocity differentials of airflow over the film will generate pressure changes which curve the flow and set up vortices. As these vortices propagate along the length of the film, they generate centrifugal forces which induce tension in the film; and this tension opposes and ultimately limits the amplitudes of the film flutter. Thus when air flows over the flexible film with induced tension, there is a dynamic of lift forces normal to the film surface and an opposing drag force due to the tensioned edge.

Figure 3:
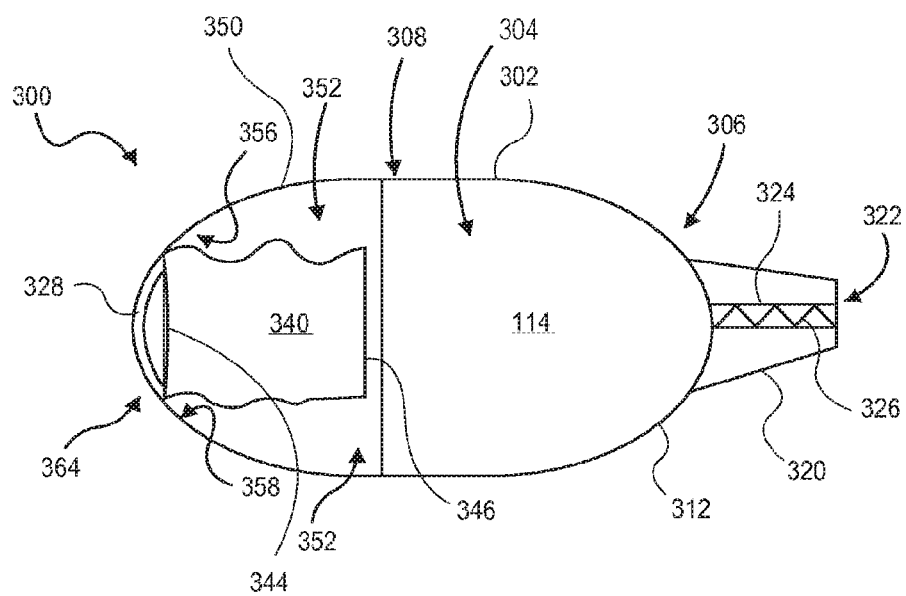
FIG. 3 is a schematic representation of a top cross-sectional view of an exemplary inhaler in accordance with various aspects of the disclosure.
Figure 4:
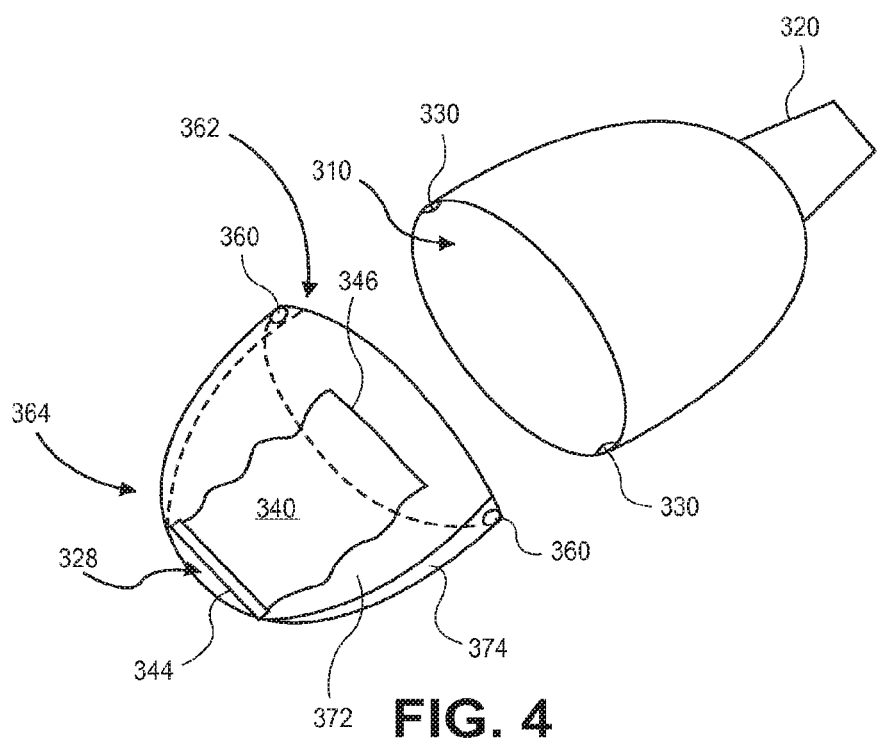
FIG. 4 is an exploded view of the inhaler of FIG. 3.

Referring now to FIGS. 3 and 4, according to various aspects, an exemplary inhaler assembly 300 may include a first housing 302 and a second housing 350. The first housing 302 defines a chamber 304. A proximal end 306 of the housing 302 may include a mouthpiece 320. In some aspects, the mouthpiece 320 may comprise a separate structure affixed to an outer wall 312 of the housing 302. In some aspects, the mouthpiece 320 and housing 302 may comprise a single piece of unitary construction.

The mouthpiece 320 may include an opening 322 providing fluid communication between the chamber 304 and the outside of the housing 302 (i.e., ambient air). The opening 322 may be shaped as an oval, a circle, a triangle, or any other desired shape. The mouthpiece 320 may have a shape that facilitates pursing of a patient's lips over the mouthpiece 320 and creating a seal between the lips and the mouthpiece 320.

In various aspects, the inhaler 300 may include a nozzle 324 between the chamber 304 and the opening 322. According to various aspects, the nozzle 324 may extend from the opening 322, through the mouthpiece 320, and into the chamber 304. In some aspects, the nozzle 324 may comprise at least one helical tube 326 through which air and powder can be inhaled. The helical tube 326 can be configured to increase the turbulence in the air that flows through the nozzle 324. According to various aspects, the mouthpiece 320 and/or the housing 302 may include a mesh, screen, or the like (not shown) to prevent undesirably large particles, such as, for example, carrier particles, from exiting the inhaler assembly 300 and entering a user's mouth and/or airways.

In accordance with various aspects, a distal end 308 of the housing 302 may include an opening 310 and a coupling mechanism 330. The coupling mechanism 330 may comprise any known structure for coupling two housings to one another, such as, for example, a snap fit, a friction/interference fit, a screw fit, and the like.

The second housing 350 defines a chamber 352 having an open proximal end 362. The proximal end 362 of the second housing 350 may include a coupling mechanism 360 structured and arranged to cooperate with the coupling mechanism 330 of the first housing 302 to couple the first and second housings 302, 350 to one another. When the first and second housings 302, 350 are coupled together, the chambers 304, 352 are in fluid communication with one another. A distal end 364 of the second housing 350 may include one or more airflow inlets 328 providing fluid communication between a chamber 352 and ambient air outside the housing 350.

A flutter element 340 may extend across a center region 354 of the chamber 352 at or near the inlets and at or near the wall of the distal end 364 of the housing 350. In some aspects, the flutter element 340 may extend between opposing inner walls 356, 358 of the second housing 350. According to various aspects, the airflow inlets 328 may be shaped as elongated slots, and the flutter element 340 may be arranged such that the planar surfaces of the flutter element 340 extend substantially parallel with the longitudinal direction of the elongated slot. As such, airflow through the chamber 352 may flow above and/or below the flutter element 340 depending on whether the flutter element 340 is positioned at the bottom of the slot, the middle of the slot, or the top of the slot.

The flutter element 340 may be pre-coated with a dose of a medicament, for example, a dose of powdered medicament, and the chamber 352 of the second housing 350 may comprise a region for dispensing a dose of medicament into airflow through the inhaler assembly 300. The flutter element 340 may be pre-coated with a dose of a medicament, for example, a dose of powdered medicament, and the chamber 352 may comprise a region for dispensing a dose of medicament into airflow through the inhaler assembly 300. In some aspects, the powdered particles are tightly bound to the flutter element 340 such that the particles remain substantially on the flutter element 340 until used for an inhalation dose. Contact of the coated flutter element 340 with surfaces of the inhaler assembly and/or packaging should not impact the dosage.

The term "medicament" as used throughout this disclosure may include one or more drugs and/or compositions for treatment. For example, the flutter element 340 may be coated with a medicament containing two or more drug mixed together. In some aspects, two or more drugs may be coated onto the flutter element 340 in a side-by-side manner or any other pattern. In some aspects, the chamber 352 may be divided into compartments, and each compartment may contain a separate flutter element 340 with the same or different medicament and/or drug(s) coated thereon. In some aspects, the chamber 352 may be divided into compartments, and each compartment may contain a portion of the same flutter element 340, with each portion having the same or different medicament and/or drug(s) coated thereon.

According to some aspects, the flutter element 340 may comprise a membrane 342, for example, a thin elastic membrane. In accordance with some aspects, the flutter element 340 may comprise a membrane, a film, a reed, a sheet, a panel, or a blade. The flutter element may be manufactured of materials comprising polymers, thin metals, and/or metal-coated polymers. It should be appreciated that the flutter element 340 can be made thicker and/or more rigid to reduce the degree to which the flutter element 340 will droop in the absence of airflow due to the force of gravity. A more rigid and/or thicker flutter element 340 may result in less flutter insofar as amplitude and wavelength, but at a higher frequency.

According to various aspects, a first end 344 of the element 340 is proximate the airflow inlet 328 at the distal end 364 of the second housing 350. The first end 344 of the element 340 is held substantially taut across the chamber 352. A second end 346 of the element 340, opposite to the first end 344, is left free as it extends towards the proximal end 306 of the first housing 302. Thus, the element 340 is free to flutter, for example, like a flag, as air flows through the chamber 352 from the airflow inlet 328 to the chamber 304 of the first housing 302 and eventually to the mouthpiece 320.

It should be appreciated that the first end 344 of the element 340 may be held by any known structure and method. For example, the element 340 may be coupled to the second housing 350 in tension via clipping, gluing, adhering, bonding, molding, fusing, or the like. In some aspects, as shown in FIG. 4, the second housing 350 may comprise a first housing member 372 and a second housing member 374 structured to be coupled together in any known manner, such as for example, a snap fit, or friction/interference fit relationship. One skilled in the art would recognize that an element 340 pre-coated with a dose of dry powder medicament can be press-fit between the first and second housing members 372, 374 when they are coupled together to hold the first end 344 of the element 340 in a substantially taut configuration, while the second end 346 is left free to flutter in airflow or droop in the absence of airflow.

It should be appreciated that the second housing 350 of the inhaler assembly 300 may comprise a single powder dose such that the second housing 350 may be decoupled from the first housing 302 and disposed of after a single use, while the first housing 302 may be reusable. In some aspects, the second housing 350 may include multiple compartments, each containing a separate flutter element 340 or a portion of the same flutter element 340, and the flutter element in each compartment may be coated with the same or different drugs and/or medicament. A new second housing containing a single powder dose may be packaged to maintain the dose in a sterile condition according to government regulations. When another dose is to be dispensed, a user removes the new second housing from the packaging and attaches the new second housing to the first housing 302 for use.

It should also be appreciated that the flutter elements 140, 340, in some aspects, may be wrapped on a spool. The flutter element may be coated with one or more drugs and/or medicament in any manner. An inhaler in accordance with such aspects may include a delivery spool and a take-up spool working in cooperation with a mechanical and/or electrical drive system for moving a coated region of the flutter element into position for dispersal into the airflow through the inhaler, as would be understood by persons skilled in the art. Inhalers according to such aspects may further include a cutting member for removing the tension at a proximal end of the flutter element so that the inhaler may operate similar to the previously described embodiments.

In operation, a method for dispensing powder by inhalation using any of the aforementioned exemplary dry powder inhaler apparatuses may begin with a patient pursing his/her lips around the mouthpiece and inhaling. As the patient inhales, air is sucked into the inhaler through one or more airflow inlets at the distal end of the inhaler. The inhaled air flows over the flutter element causing the element to flutter. The vibration or flutter of the element disperses a dose of powdered medicament from the element into the airflow. The combined flow of air and powder then flow into the distal end of the airflow nozzle and the mouthpiece. The combined flow of air and powder leave the mouthpiece and enter the patient's mouth and respiratory tract. The airflow modifiers and/or the helical shape of the nozzle may increase the turbulence of the airflow to better aerosolize and break up the powdered dose of medicament into smaller particles, thus maximizing the dose received by the patient and allowing the smaller particles to pass further into the respiratory tract.

EXAMPLE 1

Effect of Flow Rate

The aerosol properties of the prototype are determined by a Next Generation Impactor (NGI). The device geometry used in this first example is a truncated cone-single barrel (TC-SB) with inlet diameter of 0.4 cm and outlet diameter of 0.6 mm and length of 2.5 cm. The film (i.e., flutter membrane) is a polyolefin film (length=2.8 cm, width=0.3 cm, and a thickness of 85 microns). The flow rates studied are 30 lpm and 60 lpm. The drug used here is ciprofloxacin and is analyzed analytically using a UVvis spectrophotometer.

Figure 5:
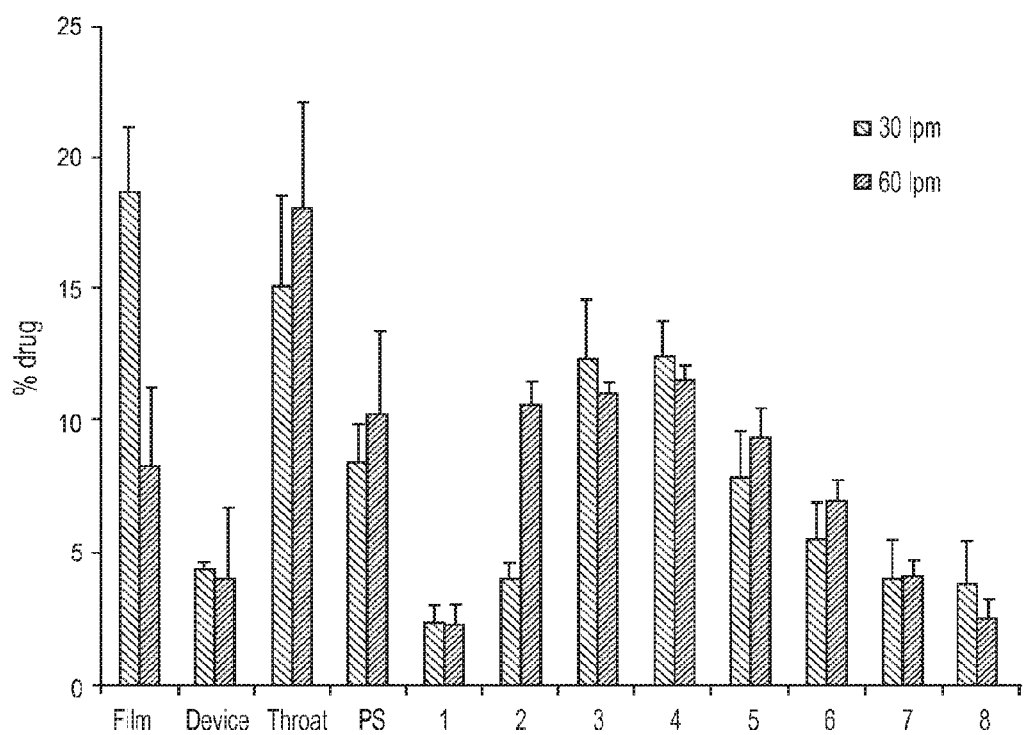
FIG. 5 is a graph illustrating the dispersion profile of drug microparticles from a flutter element structured and arranged in accordance with exemplary apparatuses and methods of the disclosure.

As shown in FIG. 5, more drug is removed from the film at 60 lpm than 30 lpm. The respirable fraction (RF) at 60 lpm is 56.75±2.73% compared to that of 30 lpm which is 46.62±6.34%. The fine particle fraction (FPF) at 60 lpm and 30 lpm is statistically similar at 65.06±6.84% and 60.65±7.64%.

EXAMPLE 2

Effect of Device Geometry

The device geometry may play an important role in drug dispersion. The device geometries used in this example are a truncated cone-singe barrel (TCSB), truncated cone-double barrel (TC-DB, made of two single barrel), cylindrical chamber (CC, diameter of=0.6 cm and length=2.5 cm), Slit nozzle (SN, rectangular nozzle—3 cm by 1 mm). The drug used here is ciprofloxacin and is analyzed analytically using a UVvis spectrophotometer. The flow rate is 60 lpm.

Figure 6:
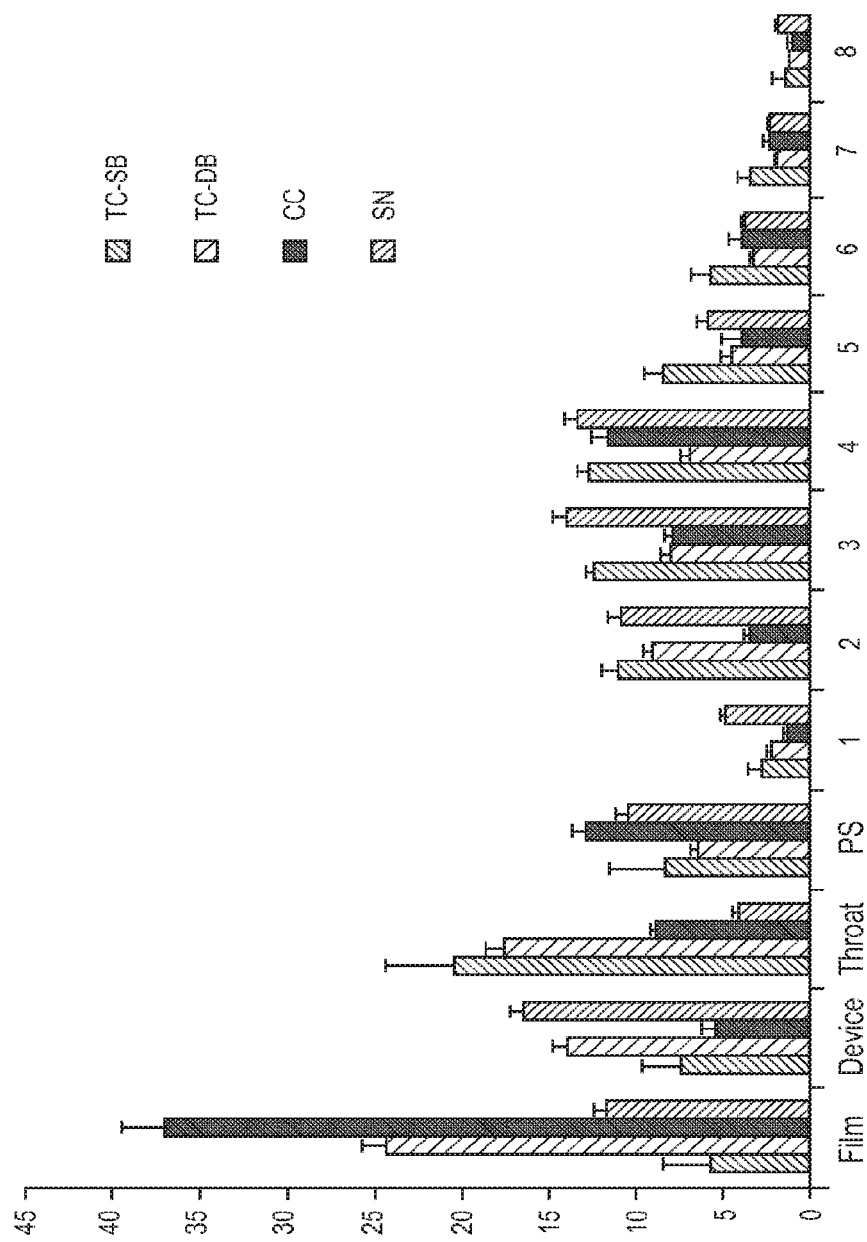
FIG. 6 is a graph illustrating the dispersion profile of drug microparticles from a flutter element structured and arranged in accordance with exemplary apparatuses and methods of the disclosure.

As shown in FIG. 6, more drug is removed from the film in TC-single barrel than double barrel. However there is more throat deposition in TC-single barrel. The Cylindrical chamber has most drug removed from the film. This suggests the magnitude of dynamic flutter forces is lowest in cylindrical chamber. More device deposition is noticed in slit nozzle. The FPF and RF are shown for the following devices are shown in the table below.

TABLE 1

FPF and RF percentages for various device geometries.

| Device | FPF (%) | RF (%) |
|---|---|---|
| Truncated Cone-SB | 65.06 ± 6.84 | 56.75 ± 2.73 |
| Truncated Cone-DB | 57.65 ± 2.91 | 36.53 ± 1.78 |
| Cylindrical Chamber | 59.91 ± 2.05 | 34.49 ± 2.49 |
| Slit Nozzle | 72.73 ± 3.63 | 52.26 ± 2.61 |

EXAMPLE 3

Effect of Field Dimensions (Length)

In the slit nozzle device, the effect of film length is studied. The two lengths that are studied are 3 cm and 1.5 cm. The drug used here is ciprofloxacin and is analyzed analytically using UVvis spectrophotometer. The flow rate is 60 lpm.

Figure 7:
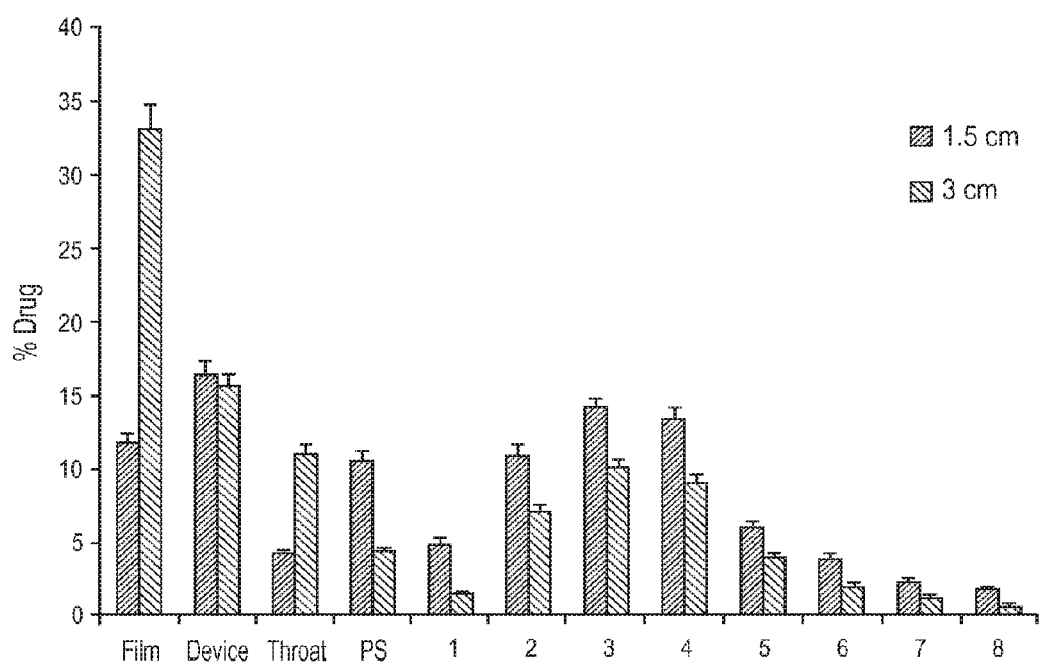
FIG. 7 is a graph illustrating the dispersion profile of drug microparticles from a flutter element structured and arranged in accordance with exemplary apparatuses and methods of the disclosure.

As shown in FIG. 7, as the length is increased, drug removal from the film is decreased and a higher percentage drug is deposited in the throat. RF is higher when we use a 1.5 cm film compared to that of 3 cm length, as shown in the table below.

TABLE 2

FPF and RF percentages for various film lengths.

| Length of film | FPF (%) | RF (%) |
|---|---|---|
| 1.5 cm | 72.73 ± 3.63 | 52.26 ± 2.61 |
| 3 cm | 67.14 ± 3.36 | 34.38 ± 1.72 |

EXAMPLE 4

Effect of Field Dimensions (Film Thickness)

In the slit nozzle device, the effect of film thickness is studied. The two thicknesses that are studied are 0.085 mm and 0.150 mm. The drug used here is ciprofloxacin and is analyzed analytically using a UVvis spectrophotometer. The flow rate is 60 lpm.

Figure 8:
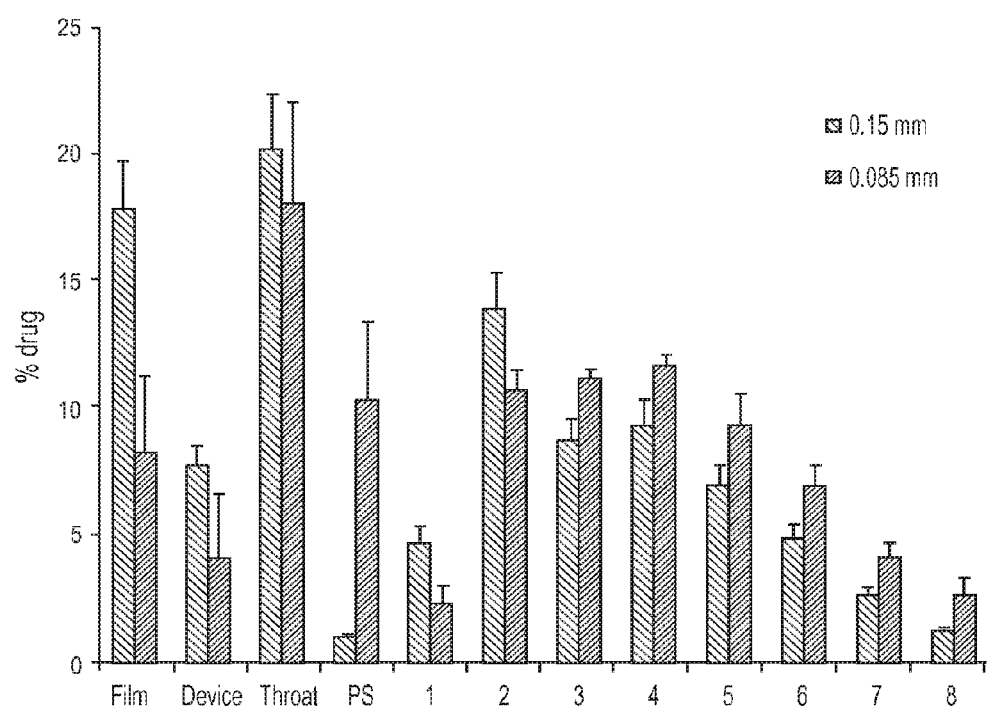
FIG. 8 is a graph illustrating the dispersion profile of drug microparticles from a flutter element structured and arranged in accordance with exemplary apparatuses and methods of the disclosure.

As shown in FIG. 8, the percentage of drug remaining in the film is higher for the thicker film. This suggests that the film is more rigid at higher thickness resulting in lower magnitude flutter forces at the same flow rate, as supported by Table 3 below.

TABLE 3

FPF and RF percentages for various film thicknesses.

| Thickness of film | FPF (%) | RF (%) |
|---|---|---|
| 0.085 mm | 65.06 ± 6.84 | 56.76 ± 2.74 |
| 0.15 mm | 64.79 ± 4.86 | 48.14 ± 3.61 |

EXAMPLE 5

Various critical dimensions of the design illustrated in FIG. 4 were assessed for their effect on device performance (Table 4a). The device was manufactured using normal resolution stereo lithography in 0.004-inch layers and post-processed for biocompatibility for passing USP class VI testing. The device was manufactured out of a biocompatible, low viscosity photopolymer. The aerosol dispersion characteristics of the prototype have been determined using the Next Generation Impactor (NGI). The flow rate of operation was 60 lpm. The film used in these studies was a 0.085 mm polyolefin film (MPF, Dow Chemicals ltd.). The model drug used in the study was ciprofloxacin and was analyzed analytically using UV-vis spectrophotometer at 280 nm.

Parameters Determined:

The following parameters were determined from the NGI dispersion data: (1) Fine Particle Fraction (FPF)—the percentage of drug deposition from stages 3 to 8 with respect to total emitted dose (throat to stage 8). (2) Fine Particle Dose (FPD)—the amount of drug deposited in stage 3 to stage 8. (3) Respirable Fraction (RF)—the percentage of drug deposition in stages 3 to 8 with respect to the total dosage. (4) Mean Mass Aerodynamic Diameter (MMAD).

Table 4a details the aerosol properties of the prototypes as the depth and angle of opening (q) of the prototype are varied at a constant length. At a constant length, the aerosol performance changes significantly with depth. The FPF decreases by approximately 15% as the inlet depth of the prototype is doubled. The performance of the device (FPF and RF) decreases by a modest 5% as the angle of inlet is doubled.

TABLE 4a

Aerosol Properties as a function of dimension @ constant length (L).

| Depth (D, mm) | Length (L, mm) | Angle ($\theta$) | FPF (%) | RF (%) | FPD (mcg) | MMAD (mm) |
|---|---|---|---|---|---|---|
| 1 | 40 | 5.75 | 50.42 ± 1.48 | 40.90 ± 1.89 | 471.73 ± 3.58 | 2.86 ± 0.02 |
| 2 | 40 | 5.75 | 34.57 ± 1.21 | 24.84 ± 1.82 | 310.23 ± 13.78 | 3.37 ± 0.11 |
| 1 | 40 | 11.5 | 45.67 ± 3.01 | 36.24 ± 2.55 | 384.2 ± 30.65 | 3.29 ± 0.2 |
| 2 | 40 | 11.5 | 28.24 ± 0.83 | 20.2 ± 0.84 | 294.52 ± 23.43 | 3.72 ± 0.11 |

TABLE 4b

Aerosol Properties as a function of dimension@ constant angle (q).

| Depth (D, mm) | Length (L, mm) | Angle ($\theta$) | FPF (%) | RF (%) | FPD (mcg) | MMAD (mm) |
|---|---|---|---|---|---|---|
| 1 | 40 | 5.75 | 58.21 ± 3.65 | 47.56 ± 4.42 | 503.24 ± 43.77 | 2.48 ± 0.04 |
| 2 | 40 | 5.75 | 38.21 ± 3.61 | 27.65 ± 4.36 | 323.91 ± 25.37 | 2.98 ± 0.04 |
| 1 | 20 | 5.75 | 49.87 ± 1.12 | 41.71 ± 1.77 | 545.64 ± 114.9 | 2.81 ± 0.13 |
| 2 | 20 | 5.75 | 35.72 ± 3.13 | 25.68 ± 1.71 | 288.07 ± 16.40 | 3.15 ± 0.02 |

Table 4b details the aerosol properties of the prototypes as the depth and length of the prototype are varied at a constant angle of opening. At a constant angle of opening (q), the aerosol performance is significantly affected by both the depth (D) as well as the length of the prototype. An increase in depth results in decrease in aerosol performance and an increase in length results in the increase of aerosol performance.

The effect of loaded dose on the film on the aerosol dispersion is further noted in Table 5. The two different amounts of loaded dose on the prototype (length—40 mm, depth—1 mm and q—5.75°) were 5647.12±437.88 mg (high dosage) and 1058.62±21.61 mg (low dosage). For the higher loaded dose, there was a significantly higher deposition of drug in the throat, pre-separator, stage 1 and lower deposition in the final three stages. This is due to the fact drug particles were dispersed as agglomerates resulting in increased deposition in the throat, pre-separator area. A FPD of approximately 2350 mg could be delivered using the high loaded dose.

TABLE 5

Aerosol Properties as a function of dosage.

| | Low dosage | High Dosage |
|---|---|---|
| FPF (%) | 58.20 ± 3.65 | 46.54 ± 3.65 |
| RF (%) | 47.56 ± 4.42 | 40.49 ± 4.42 |
| FPD (mg) | 610.65 ± 40.92 | 2354.66 ± 330.56 |

The flutter based model prototype was capable of producing significant aerosol dispersion of nearly 58% FPF and 47.5% RF. The performance of the device could be optimized by the manipulation of the dimensions of the prototype. A maximum fine particle dose (FPD) of up to 2350 mg of drug using high dosage films was achieved.

The terminology used herein is for the purpose of describing particular embodiments only and is not intended to be limiting of the invention. As used herein, the singular terms "a," "an," and "the" are intended to include the plural forms as well, unless the context clearly indicates otherwise. It will be further understood that the terms "comprises" and/or "comprising," when used in this specification, specify the presence of the stated features, integers, steps, operations, elements, and/or components, but do not preclude the presence or addition of one or more other features, integers, steps, operations, elements, components, and/or groups thereof.

It will be apparent to those skilled in the art that various modifications and variations can be made in the inhalers and methods of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A dry powder inhaler for delivering medicament to a patient, the dry powder inhaler comprising:
    a housing defining a chamber for receiving a dose of powdered medicament;
    an inhalation port in fluid communication with the chamber;
    an airflow inlet at a distal end of the chamber providing fluid communication between the chamber and an exterior of the housing;
    an elastic planar flutter element in the chamber, the elastic planar flutter element having substantially planar outer surfaces, a tensioned distal end held substantially taut across the chamber proximate to the airflow inlet, and a free proximal end opposite to the distal end and downstream of the airflow inlet; and
    a dose of powdered medicament coated onto and tightly bound to at least a portion if at least one of the substantially planar outer surfaces of the elastic planar flutter element,
    wherein an airflow through the chamber induces vibrations in the elastic planar flutter element sufficient to detach the dose of powdered medicament from the at least one of the substantially planar outer surfaces and aerosolize the dose of powdered medicament into the airflow.

2. The dry powder inhaler of claim 1, wherein the elastic planar flutter element comprises at least one of a membrane, a reed, a sheet, a panel, and a blade.

3. The dry powder inhaler of claim 1, wherein the elastic planar flutter element is made of a material comprising at least one of a polymer, a metal, and a metal-coated polymer.

4. The dry powder inhaler of claim 1, further comprising:
    a mouthpiece including the inhalation port; and
    a nozzle between the chamber and the inhalation port.

5. The dry powder inhaler of claim 4, wherein the nozzle comprises a helical-shaped conduit.

6. The dry powder inhaler of claim 1, wherein the distal end of the elastic planar flutter element extends across the chamber in a direction substantially perpendicular to a path of airflow from the airflow inlet to the inhalation port.

7. The dry powder inhaler of claim 1, wherein the inhalation port is at a first end of the housing and the airflow inlet is at a second end of the housing substantially opposite to the first end of the housing.

8. The dry powder inhaler of claim 1, comprising a plurality of airflow inlets providing fluid communication between the chamber and an exterior of the housing.

9. The dry powder inhaler of claim 8, wherein the plurality of airflow inlets converge toward one another in a direction of a center region of the chamber.

10. The dry powder inhaler of claim 8, wherein the tensioned distal end of the elastic planar flutter element is held substantially taut across the chamber proximate to one of the plurality of airflow inlets.

11. The dry powder inhaler of claim 1, wherein the tensioned distal end of the elastic planar flutter element is positioned at the airflow inlet.

12. The dry powder inhaler of claim 11, comprising a plurality of airflow inlets providing fluid communication between the chamber and the exterior of the housing, wherein the tensioned distal end of the elastic planar flutter element is positioned at one of the plurality of airflow inlets.

13. The dry powder inhaler of claim 1, wherein the airflow inlet comprises at least one elongated slot, wherein the substantially planar outer surfaces of the elastic planar flutter member is substantially parallel with a longitudinal direction of the at least one elongated slot.

14. A method for delivering medicament to a patient, the method comprising:
    tensioning a distal end of an elastic planar flutter element having substantially planar outer surfaces, at least a portion of at least one of the substantially planar outer surfaces having a dose of powdered medicament coated onto and tightly bound thereto, wherein the tensioning is such that the distal end of the elastic planar flutter element is substantially taut across a dosing chamber proximate to an airflow inlet at a distal end of the dosing chamber while permitting a proximal end of the elastic planar flutter element to remain free of tension;
    exposing the elastic planar flutter element to a flow of air through the airflow inlet to induce vibrations in the elastic planar flutter element, wherein the vibrations detach the dose of powdered medicament from the at least one of the substantially planar outer surfaces and aerosolize the dose of powdered medicament into the flow of air; and
    directing the flow of air with the aerosolized dose of powdered medicament to an outlet port from the dosing chamber.

15. The method of claim 14, wherein the airflow inlet comprises at least one elongated slot, wherein the substantially planar outer surfaces of the elastic planar flutter member is substantially parallel with a longitudinal direction of the at least one elongated slot.

16. A dry powder inhaler comprising:
    a housing defining a chamber and an inhalation port in fluid communication with the chamber;
    an elastic planar flutter element in the chamber, the elastic planar flutter element having substantially planar outer surfaces, a tensioned distal end held substantially taut across the chamber proximate an airflow inlet at a distal end of the chamber, and a free proximal end opposite the distal end and downstream of the airflow inlet, wherein at least a portion of at least one of the substantially planar outer surfaces are coated with a dose of powdered medicament tightly bound to the at least one of the substantially planar outer surfaces, the elastic planar flutter element being configured to vibrate in response to airflow through the chamber, wherein vibrations of the elastic planar flutter member induced by the airflow cause the dose of powdered medicament to detach from the at least one of the substantially planar outer surfaces and aerosolize into the airflow.

17. The dry powder inhaler of claim 16, further comprising a mouthpiece, the mouthpiece including the inhalation port and a nozzle, the nozzle comprising a helical-shaped conduit between the chamber and the inhalation port.

18. The dry powder inhaler of claim 16, wherein the airflow inlet comprises at least one elongated slot, wherein the substantially planar outer surfaces of the elastic planar flutter member is substantially parallel with a longitudinal direction of the at least one elongated slot.

* * * * *

UNITED STATES PATENT AND TRADEMARK OFFICE
CERTIFICATE OF CORRECTION

PATENT NO. : 9,492,625 B2
APPLICATION NO. : 13/505402
DATED : November 15, 2016
INVENTOR(S) : Smyth et al.

It is certified that error appears in the above-identified patent and that said Letters Patent is hereby corrected as shown below:

In the Claims

In Column 13, Line 44, in Claim 1, delete "if" and insert --of--, therefor

Signed and Sealed this
Seventeenth Day of April, 2018

Andrei Iancu
*Director of the United States Patent and Trademark Office*